(12) United States Patent
Riggs-Sauthier et al.

(10) Patent No.: US 8,389,759 B2
(45) Date of Patent: Mar. 5, 2013

(54) OLIGOMER-ANTICHOLINERGIC AGENT CONJUGATES

(75) Inventors: Jennifer Riggs-Sauthier, Huntsville, AL (US); Bo-Liang Deng, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 569 days.

(21) Appl. No.: 12/530,424

(22) PCT Filed: Mar. 12, 2008

(86) PCT No.: PCT/US2008/003296
§ 371 (c)(1),
(2), (4) Date: Feb. 17, 2010

(87) PCT Pub. No.: WO2008/112261
PCT Pub. Date: Sep. 18, 2008

(65) Prior Publication Data
US 2010/0168232 A1    Jul. 1, 2010

Related U.S. Application Data

(60) Provisional application No. 60/906,329, filed on Mar. 12, 2007.

(51) Int. Cl.
*C07C 69/76* (2006.01)
*C07C 69/74* (2006.01)
(52) U.S. Cl. ...................................... 560/101; 560/118
(58) Field of Classification Search .................. None
See application file for complete search history.

(56) References Cited

U.S. PATENT DOCUMENTS

| 5,672,662 A | 9/1997 | Harris et al. |
| 6,815,530 B2 | 11/2004 | Ekwuribe et al. |
| 6,835,802 B2 | 12/2004 | Ekwuribe et al. |
| 2005/0136031 A1 | 6/2005 | Bentley et al. |

FOREIGN PATENT DOCUMENTS

| EP | 0 452 179 | 10/1991 |
| WO | 99/64043 | 12/1999 |
| WO | 02/098949 | 12/2002 |
| WO | 2005/058367 | 6/2005 |
| WO | WO 2008/112286 | 9/2008 |

OTHER PUBLICATIONS

Zalipsky et al, European Polymer Journal, Attachment of Drugs to Polyethylene Glycols, 1983, 19(12), pp. 1177-1183.*
Zaragoza Dorwald, Side Reactions in Organic Synthesis, Wiley-VCH Verlag GmbH & Co. KGaA, Weinheim, Preface. p. IX.*
Chen, et al., "Synthesis and Properties of ABA Amphiphiles", J. Org. Chem., vol. 64, pp. 6870-6873, (1999).
Ertl, et al., "Fast Calculation of Molecular Polar Surface Area as a Sum of Fragment-Based Contributions and Its Application to the Prediction of Drug Transport Properties", J. Med. Chem., vol. 43, pp. 3714-3717, (2000).

Greenwald, et al., "Poly(ethylene glycol) Conjugated Drugs and Prodrugs: A Comprehensive Review", Crit. Rev. in Therap. Drug Carr. Sys., vol. 17, No. 2, pp. 101-161, (2000).
Hegde, et al., "Functional role of M2 and M3 muscarinic receptors in the urinary bladder of rats in vitro and in vivo", Br. J. of Pharm., vol. 120, pp. 1409-1418, (1997).
Kelder, et al., "Polar Molecular Surface as a Dominating Determinant for Oral Absorption and Brain Penetration of Drugs", Pharm. Res., vol. 16, No. 10, pp. 1514-1519, (1999).
Weiner, et al., "Atropine attached to polyethlene Glycols", Eur. J. Med. Chem., vol. 11, No. 6, pp. 525-526, (1976).
Zalipsky, et al., "Attachment of Drugs to Polyethylene Glycols", Eur. Polym. J., vol. 19, No. 12, pp. 1177-1183, (1983).
PCT International Search Report corresponding to PCT Application No. PCT/US2008/003296 date of mailing Aug. 4, 2008.
PCT International Preliminary Report on Patentability corresponding to PCT Application No. PCT/US2008/003296 date of issuance Sep. 15, 2009.
Enzon Pharmaceuticals, Macromolecular Engineering Technologies, pp. 1-14, (2004).
NEKTAR™—Transforming Therapeutics, Nektar Molecule Engineering: Polyethylene Glycol and Derivatives for Advanced PEGylation, pp. 1-20, Catalog—2003, (Jul. 2003).
NEKTAR™—Transforming Therapeutics, Nektar Advanced PEGylation: Polyethylene Glycol and Derivatives for Advanced PEGylation, pp. 1-24, Catalog—2004, (Jul. 2004).
NOF Corporation, "PEG Derivatives, Phospholipid and Drug Delivery Materials for Pharmaceuticals", pp. 1-46, Catalogue 2003—1st, (Jan. 2003).
NOF Corporation, "PEG Derivatives, Phospholipid and Drug Delivery Materials for Pharmaceuticals", pp. 1-50, Catalogue 2003—2nd, (Mar. 2004).
NOF Corporation, "PEG Derivatives, Phospholipids and Drug Delivery Materials for Pharmaceutical Products and Formulations", pp. 1-59, Catalogue Ver. 8, (Apr. 2006).
Polypure, Products; PEG amines; PEG acids and amino acids; PEG thiols and disulfides; BIOTINS, (Apr. 2004).
Polypure, Products; PEG amines; PEG acids and amino acids; PEG thiols and disulfides; BIOTINS, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™ (dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, pp. 1-49, (Catalog—Mar. 1995).

(Continued)

*Primary Examiner* — Paul A Zucker
(74) *Attorney, Agent, or Firm* — Mark A. Wilson

(57) ABSTRACT

The invention provides anticholinergic agents that are chemically modified by covalent attachment of a water-soluble oligomer. A conjugate of the invention, when administered by any of a number of administration routes, exhibits characteristics that are different as compared to the characteristics of the anticholinergic agent not attached to the water-soluble oligomer.

16 Claims, No Drawings

OTHER PUBLICATIONS

Shearwater Polymers, Inc., Polyethylene Glycol and Derivatives, pp. 1-53, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, pp. 1-17, (Catalog—Jul. 2001).
European Communication corresponding to European Patent Application No. 08 726 767.0 dated Jun. 2, 2010.
European Summons to Attend Oral Proceedings corresponding to European Patent Application No. 08 726 767.0 dated Apr. 24, 2012.

* cited by examiner

OLIGOMER-ANTICHOLINERGIC AGENT CONJUGATES

CROSS REFERENCE TO RELATED APPLICATIONS

This application is a 35 U.S.C §371 application of International Application No. PCT/US2008/003296, filed Mar. 12, 2008, designating the United States, which claims the benefit of priority under 35 U.S.C. §119(e) to U.S. Provisional Application Ser. No. 60/906,329, filed Mar. 12, 2007, both of which are incorporated herein by reference in their entireties.

FIELD OF THE INVENTION

This invention provides (among other things) chemically modified small molecule anticholinergic agents that possess certain advantages over small molecule anticholinergic agents lacking the chemical modification. The chemically modified small molecule anticholinergic agents described herein relate to and/or have application(s) in (among others) the fields of drug discovery, pharmacotherapy, physiology, organic chemistry and polymer chemistry.

BACKGROUND OF THE INVENTION

The spasmolytic effects of anticholinergic agents acting on muscarinic receptors have been used for the treatment of patients suffering from urgency, frequency, urinary leakage, urge incontinence, and dysuria, among other maladies. It is believed these agents exert a nonspecific direct relaxant effect on smooth muscle. As a consequence, administration of these muscarinic receptor antagonists results in decrease spasm of the gastrointestinal tract, biliary tract, ureter, and uterus.

The broad range of pharmacological activity of anticholinergic agents, however, often results in deleterious effects. For example, administration of oxybutynin—which is indicated for bladder instability—is associated with dizziness and somnolence. In addition, use of anticholinergic agents by patients is often associated with dry mouth.

It may be that one or more side effects (such as dizziness and somnolence) associated with the administration of anticholinergic agents is the result of the anticholinergic agent reaching the central nervous system. Thus, it would advantageous to have an anticholinergic agent that maintained its peripheral effects yet was able to avoid reaching the central nervous system.

The present invention seeks to address this and other needs in the art.

SUMMARY OF THE INVENTION

In one or more embodiments, a compound is provided, the compound comprising a residue of an anticholinergic agent covalently attached, either directly or through one or more atoms, (preferably via a stable linkage) to a water-soluble, non-peptidic oligomer.

In one or more embodiments, a compound is provided, the compound comprising a residue of an anticholinergic agent covalently attached, either directly or through one or more atoms, (preferably via a stable linkage) to a water-soluble, non-peptidic oligomer, wherein the anticholinergic agent is encompassed by the following formula:

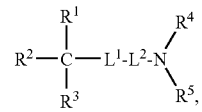

(Formula I)

wherein:

$R^1$ is selected from the group consisting of H, OH, and an organic radical, preferably $R^1$ is selected from the group consisting of —H, —OH, —CH$_2$OH, —CH$_3$, cyclopentyl, 1-hydroxyl cyclopentyl, cyclohexyl, and aromatic-containing organic radical (such as phenyl);

either (i) $R^2$ is selected from the group consisting of —H, —OH, and an organic radical [preferably $R^2$ is selected from the group consisting of —H, —OH, —CH$_2$OH, —CH$_3$, cyclopentyl, 1-hydroxyl cyclopentyl, cyclohexyl, and aromatic-containing organic radical (such as phenyl)], and $R^3$ is selected from the group consisting of H, OH, and an organic radical, [preferably $R^3$ is selected from the group consisting of —H, —OH, —CH$_2$OH, —CH$_3$, cyclopentyl, 1-hydroxyl cyclopentyl, cyclohexyl, and aromatic-containing organic radical (such as phenyl)], or (ii) $R^2$ and $R^3$ are combined to form a cyclo, such as a cyclohexyl;

with the proviso that at least one of $R^1$ and $R^3$ is an aromatic-containing organic radical (such as phenyl);

$L^1$ is —O—, —C(O)O—, —OC(O)—, —C(O)—;

$L^2$ is a $C_{2-4}$-containing hydrocarbon linker, heterocyclo (incorporating the N of Formula I), biheterocyclo (incorporating the N of Formula I);

$R^4$ is an organic radical, preferably —CH$_3$ or —CH$_2$CH$_3$; and $R^5$ is an organic radical, preferably CH$_3$ or CH$_2$CH$_3$, and further wherein the amine of Formula I is optionally charged (e.g., a quaternary nitrogen as a result of a CH$_3$ group being bound to the amine).

In one or more embodiments of the invention, a composition is provided, the composition comprising a compound comprising a residue of an anticholinergic agent covalently attached, either directly or through one or more atoms, (preferably via a stable linkage) to a water-soluble, non-peptidic oligomer; and, optionally, a pharmaceutically acceptable excipient.

In one or more embodiments of the invention, a dosage form is provided, the dosage form comprising a compound comprising a residue of an anticholinergic agent covalently attached, either directly or through one or more atoms, (preferably via a stable linkage) to a water-soluble, non-peptidic oligomer In one or more embodiments of the invention, a method is provided, the method comprising covalently attaching a water-soluble, non-peptidic oligomer to a small molecule anticholinergic agent.

In one or more embodiments of the invention, a method is provided, the method comprising administering a compound comprising a residue of an anticholinergic agent covalently attached, either directly or through one or more atoms, (preferably via a stable linkage), to a water-soluble, non-peptidic oligomer.

These and other objects, aspects, embodiments and features of the invention will become more fully apparent when read in conjunction with the following detailed description.

DETAILED DESCRIPTION OF THE INVENTION

It must be noted that, as used in this specification, the singular forms "a," "an," and "the" include plural referents unless the context clearly dictates otherwise.

In describing and claiming the present invention, the following terminology will be used in accordance with the definitions described below.

"Water soluble, non-peptidic oligomer" indicates an oligomer that is at least 35% (by weight) soluble, preferably greater than 70% (by weight), and more preferably greater than 95% (by weight) soluble, in water at room temperature. Typically, an unfiltered aqueous preparation of a "water-soluble" oligomer transmits at least 75%, more preferably at least 95%, of the amount of light transmitted by the same solution after filtering. It is most preferred, however, that the water-soluble oligomer is at least 95% (by weight) soluble in water or completely soluble in water. With respect to being "non-peptidic," an oligomer is non-peptidic when it has less than 35% (by weight) of amino acid residues.

The terms "monomer," "monomeric subunit" and "monomeric unit" are used interchangeably herein and refer to one of the basic structural units of a polymer or oligomer. In the case of a homo-oligomer, a single repeating structural unit forms the oligomer. In the case of a co-oligomer, two or more structural units are repeated—either in a pattern or randomly—to form the oligomer. Preferred oligomers used in connection with present the invention are homo-oligomers. The water-soluble, non-peptidic oligomer typically comprises one or more monomers serially attached to form a chain of monomers. The oligomer can be formed from a single monomer type (i.e., is homo-oligomeric) or two or three monomer types (i.e., is co-oligomeric).

An "oligomer" is a molecule possessing from about 2 to about 50 monomers, preferably from about 2 to about 30 monomers. The architecture of an oligomer can vary. Specific oligomers for use in the invention include those having a variety of geometries such as linear, branched, or forked, to be described in greater detail below.

"PEG" or "polyethylene glycol," as used herein, is meant to encompass any water-soluble poly(ethylene oxide). Unless otherwise indicated, a "PEG oligomer" (also called an oligoethylene glycol) is one in which substantially all (and more preferably all) monomeric subunits are ethylene oxide subunits. The oligomer may, however, contain distinct end capping moieties or functional groups, e.g., for conjugation. Typically, PEG oligomers for use in the present invention will comprise one of the two following structures: "—($CH_2CH_2O$)$_n$—" or "—($CH_2CH_2O$)$_{n-1}CH_2CH_2$—," depending upon whether the terminal oxygen(s) has been displaced, e.g., during a synthetic transformation. For PEG oligomers, "n" varies from about 2 to 50, preferably from about 2 to about 30, and the terminal groups and architecture of the overall PEG can vary. When PEG further comprises a functional group, A, for linking to, e.g., a small molecule drug, the functional group when covalently attached to a PEG oligomer does not result in formation of (i) an oxygen-oxygen bond (—O—O—, a peroxide linkage), or (ii) a nitrogen-oxygen bond (N—O, O—N).

An "end capping group" is generally a non-reactive carbon-containing group attached to a terminal oxygen of a PEG oligomer. Exemplary end capping groups comprise a $C_{1-5}$ alkyl group, such as methyl, ethyl and benzyl), as well as aryl, heteroaryl, cyclo, heterocyclo, and the like. For the purposes of the present invention, the preferred capping groups have relatively low molecular weights such as methyl or ethyl. The end-capping group can also comprise a detectable label. Such labels include, without limitation, fluorescers, chemiluminescers, moieties used in enzyme labeling, colorimetric labels (e.g., dyes), metal ions, and radioactive moieties.

"Branched", in reference to the geometry or overall structure of an oligomer, refers to an oligomer having two or more polymers representing distinct "arms" that extend from a branch point.

"Forked" in reference to the geometry or overall structure of an oligomer, refers to an oligomer having two or more functional groups (typically through one or more atoms) extending from a branch point.

A "branch point" refers to a bifurcation point comprising one or more atoms at which an oligomer branches or forks from a linear structure into one or more additional arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive," with reference to a functional group present on a molecule in a reaction mixture, indicates that the group remains largely intact under conditions that are effective to produce a desired reaction in the reaction mixture.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof encompasses protected forms thereof.

A "physiologically cleavable" or "hydrolyzable" or "degradable" bond is a relatively labile bond that reacts with water (i.e., is hydrolyzed) under ordinary physiological conditions. The tendency of a bond to hydrolyze in water under ordinary physiological conditions will depend not only on the general type of linkage connecting two central atoms but also on the substituents attached to these central atoms. Such bonds are generally recognizable by those of ordinary skill in the art. Appropriate hydrolytically unstable or weak linkages include but are not limited to carboxylate ester, phosphate ester, anhydrides, acetals, ketals, acyloxyalkyl ether, imines, orthoesters, peptides, oligonucleotides, thioesters, and carbonates.

An "enzymatically degradable linkage" means a linkage that is subject to degradation by one or more enzymes under ordinary physiological conditions.

A "stable" linkage or bond refers to a chemical moiety or bond, typically a covalent bond, that is substantially stable in water, that is to say, does not undergo hydrolysis under ordinary physiological conditions to any appreciable extent over an extended period of time. Examples of hydrolytically stable linkages include but are not limited to the following: carbon-carbon bonds (e.g., in aliphatic chains), ethers, amides, urethanes, amines, and the like. Generally, a stable linkage is one that exhibits a rate of hydrolysis of less than about 1-2% per day under ordinary physiological conditions. Hydrolysis rates of representative chemical bonds can be found in most standard chemistry textbooks.

In the context of describing the consistency of oligomers in a given composition, "substantially" or "essentially" means nearly totally or completely, for instance, 95% or greater, more preferably 97% or greater, still more preferably 98% or greater, even more preferably 99% or greater, yet still more preferably 99.9% or greater, with 99.99% or greater being most preferred of some given quantity.

"Monodisperse" refers to an oligomer composition wherein substantially all of the oligomers in the composition have a well-defined, single molecular weight and defined number of monomers, as determined by chromatography or mass spectrometry. Monodisperse oligomer compositions are in one sense pure, that is, substantially comprising molecules having a single and definable number of monomers rather than several different numbers of monomers (i.e., an oligomer composition having three or more different oligomer sizes). A monodisperse oligomer composition possesses a MW/Mn value of 1.0005 or less, and more preferably, a MW/Mn value of 1.0000. By extension, a composition comprised of monodisperse conjugates means that substantially all oligomers of all conjugates in the composition have a single and definable number (as a whole number) of monomers rather than a distribution and would possess a MW/Mn value of 1.0005, and more preferably, a MW/Mn value of 1.0000 if the oligomer were not attached to the residue of an anticholinergic agent. A composition comprised of monodisperse conjugates can include, however, one or more nonconjugate substances such as solvents, reagents, excipients, and so forth.

"Bimodal," in reference to an oligomer composition, refers to an oligomer composition wherein substantially all oligomers in the composition have one of two definable and different numbers (as whole numbers) of monomers rather than a distribution, and whose distribution of molecular weights, when plotted as a number fraction versus molecular weight, appears as two separate identifiable peaks. Preferably, for a bimodal oligomer composition as described herein, each peak is generally symmetric about its mean, although the size of the two peaks may differ. Ideally, the polydispersity index of each peak in the bimodal distribution, Mw/Mn, is 1.01 or less, more preferably 1.001 or less, and even more preferably 1.0005 or less, and most preferably a MW/Mn value of 1.0000. By extension, a composition comprised of bimodal conjugates means that substantially all oligomers of all conjugates in the composition have one of two definable and different numbers (as whole numbers) of monomers rather than a large distribution and would possess a MW/Mn value of 1.01 or less, more preferably 1.001 or less and even more preferably 1.0005 or less, and most preferably a MW/Mn value of 1.0000 if the oligomer were not attached to the small molecule anticholinergic. A composition comprised of bimodal conjugates can include, however, one or more nonconjugate substances such as solvents, reagents, excipients, and so forth.

An "anticholinergic agent" is broadly used herein to refer to an organic, inorganic, or organometallic compound typically having a molecular weight of less than about 1000 Daltons (and typically less than 500 Daltons) and having some degree of activity as an anticholinergic agent. Small molecule anticholinergic agents encompass oligopeptides and other biomolecules having a molecular weight of less than about 1000.

A "biological membrane" is any membrane, typically made from specialized cells or tissues, that serves as a barrier to at least some foreign entities or otherwise undesirable materials. As used herein a "biological membrane" includes those membranes that are associated with physiological protective barriers including, for example: the blood-brain barrier (BBB); the blood-cerebrospinal fluid barrier; the blood-placental barrier; the blood-milk barrier; the blood-testes barrier; and mucosal barriers including the vaginal mucosa, urethral mucosa, anal mucosa, buccal mucosa, sublingual mucosa, rectal mucosa, and so forth. Unless the context clearly dictates otherwise, the term "biological membrane" does not include those membranes associated with the middle gastro-intestinal tract (e.g., stomach and small intestines).

A "biological membrane crossing rate," as used herein, provides a measure of a compound's ability to cross a biological membrane (such as the membrane associated with the blood-brain barrier). A variety of methods can be used to assess transport of a molecule across any given biological membrane. Methods to assess the biological membrane crossing rate associated with any given biological barrier (e.g., the blood-cerebrospinal fluid barrier, the blood-placental barrier, the blood-milk barrier, the intestinal barrier, and so forth), are known in the art, described herein and/or in the relevant literature, and/or can be determined by one of ordinary skill in the art.

A "reduced rate of metabolism" in reference to the present invention, refers to a measurable reduction in the rate of metabolism of a water-soluble oligomer-small molecule drug conjugate as compared to rate of metabolism of the small molecule drug not attached to the water-soluble oligomer (i.e., the small molecule drug itself) or a reference standard material. In the special case of "reduced first pass rate of metabolism," the same "reduced rate of metabolism" is required except that the small molecule drug (or reference standard material) and the corresponding conjugate are administered orally. Orally administered drugs are absorbed from the gastro-intestinal tract into the portal circulation and must pass through the liver prior to reaching the systemic circulation. Because the liver is the primary site of drug metabolism or biotransformation, a substantial amount of drug can be metabolized before it ever reaches the systemic circulation. The degree of first pass metabolism, and thus, any reduction thereof, can be measured by a number of different approaches. For instance, animal blood samples can be collected at timed intervals and the plasma or serum analyzed by liquid chromatography/mass spectrometry for metabolite levels. Other techniques for measuring a "reduced rate of metabolism" associated with the first pass metabolism and other metabolic processes are known in the art, described herein and/or in the relevant literature, and/or can be determined by one of ordinary skill in the art. Preferably, a conjugate of the invention can provide a reduced rate of metabolism reduction satisfying at least one of the following values: at least about 30%; at least about 40%; at least about 50%; at least about 60%; at least about 70%; at least about 80%; and at least about 90%. A compound (such as a small molecule drug or conjugate thereof) that is "orally bioavailable" is one that preferably possesses a bioavailability when administered orally of greater than 25%, and preferably greater than 70%, where a compound's bioavailability is the fraction of administered drug that reaches the systemic circulation in unmetabolized form.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced. An "alkenyl" group is an alkyl of 2 to 20 carbon atoms with at least one carbon-carbon double bond.

The terms "substituted alkyl" or "substituted $C_{q-r}$ alkyl" where q and r are integers identifying the range of carbon atoms contained in the alkyl group, denotes the above alkyl groups that are substituted by one, two or three halo (e.g., F, Cl, Br, I), trifluoromethyl, hydroxy, $C_{1-7}$ alkyl (e.g., methyl, ethyl, n-propyl, isopropyl, butyl, t-butyl, and so forth), $C_{1-7}$ alkoxy, $C_{1-7}$ acyloxy, $C_{3-7}$ heterocyclic, amino, phenoxy, nitro, carboxy, carboxy, acyl, cyano. The substituted alkyl groups may be substituted once, twice or three times with the same or with different substituents.

"Lower alkyl" refers to an alkyl group containing from 1 to 6 carbon atoms, and may be straight chain or branched, as exemplified by methyl, ethyl, n-butyl, i-butyl, t-butyl. "Lower alkenyl" refers to a lower alkyl group of 2 to 6 carbon atoms having at least one carbon-carbon double bond.

"Non-interfering substituents" are those groups that, when present in a molecule, are typically non-reactive with other functional groups contained within the molecule.

"Alkoxy" refers to an —O—R group, wherein R is alkyl or substituted alkyl, preferably $C_1$-$C_{20}$ alkyl (e.g., methoxy, ethoxy, propyloxy, benzyl, etc.), preferably $C_1$-$C_7$.

"Pharmaceutically acceptable excipient" or "pharmaceutically acceptable carrier" refers to component that can be included in the compositions of the invention in order to provide for a composition that has an advantage (e.g., more suited for administration to a patient) over a composition lacking the component and that is recognized as not causing significant adverse toxicological effects to a patient.

The term "aryl" means an aromatic group having up to 14 carbon atoms. Aryl groups include phenyl, naphthyl, biphenyl, phenanthrenyl, naphthacenyl, and the like. "Substituted phenyl" and "substituted aryl" denote a phenyl group and aryl group, respectively, substituted with one, two, three, four or five (e.g. 1-2, 1-3 or 1-4 substituents) chosen from halo (F, Cl, Br, I), hydroxy, hydroxy, cyano, nitro, alkyl (e.g., $C_{1-6}$ alkyl), alkoxy (e.g., $C_{1-6}$ alkoxy), benzyloxy, carboxy, aryl, and so forth.

An "aromatic-containing moiety" is a collection of atoms containing at least aryl and optionally one or more atoms. Suitable aromatic-containing moieties are described herein below.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent radical (e.g., $CH_3$—$CH_2$—), in certain circumstances a bivalent linking moiety can be "alkyl," in which case those skilled in the art will understand the alkyl to be a divalent radical (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for O, and 2, 4, or 6 for S, depending on the oxidation state of the S).

"Pharmacologically effective amount," "physiologically effective amount," and "therapeutically effective amount" are used interchangeably herein to mean the amount of a water-soluble oligomer-small molecule drug conjugate present in a composition that is needed to provide a threshold level of active agent and/or conjugate in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

A "difunctional" oligomer is an oligomer having two functional groups contained therein, typically at its termini. When the functional groups are the same, the oligomer is said to be homodifunctional. When the functional groups are different, the oligomer is said to be heterobifunctional.

A basic reactant or an acidic reactant described herein include neutral, charged, and any corresponding salt forms thereof.

The term "patient," refers to a living organism suffering from or prone to a condition that can be prevented or treated by administration of a conjugate as described herein, typically, but not necessarily, in the form of a water-soluble oligomer-small molecule drug conjugate, and includes both humans and animals.

"Optional" or "optionally" means that the subsequently described circumstance may but need not necessarily occur, so that the description includes instances where the circumstance occurs and instances where it does not.

As indicated above, the present invention is directed to (among other things) a compound comprising a residue of an anticholinergic agent covalently attached, either directly or through one or more atoms, (preferably) via a stable linkage to a water-soluble, non-peptidic oligomer.

In one or more embodiments of the invention, a compound is provided, the compound comprising a residue of an anticholinergic agent covalently attached via a stable or degradable linkage to a water-soluble, non-peptidic oligomer, wherein the anticholinergic agent has a structure encompassed by the following formula:

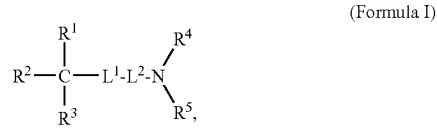

(Formula I)

wherein:

$R^1$ is selected from the group consisting of H, OH, and an organic radical, preferably $R^1$ is selected from the group consisting of —H, —OH, —$CH_2OH$, —$CH_3$, cyclopentyl, 1-hydroxyl cyclopentyl, cyclohexyl, and aromatic-containing organic radical (such as phenyl);

either (i) $R^2$ is selected from the group consisting of —H, —OH, and an organic radical [preferably $R^2$ is selected from the group consisting of —H, —OH, —$CH_2OH$, —$CH_3$, cyclopentyl, 1-hydroxyl cyclopentyl, cyclohexyl, and aromatic-containing organic radical (such as phenyl)], and $R^3$ is selected from the group consisting of H, OH, and an organic radical, [preferably $R^3$ is selected from the group consisting of —H, —OH, —$CH_2OH$, —$CH_3$, cyclopentyl, 1-hydroxyl cyclopentyl, cyclohexyl, and aromatic-containing organic radical (such as phenyl)], or (ii) $R^2$ and $R^3$ are combined to form a cyclo, such as a cyclohexyl;

with the proviso that at least one of $R^1$ and $R^3$ is an aromatic-containing organic radical (such as phenyl);

L¹ is —O—, —C(O)O—, —OC(O)—, —C(O)—;

L² is a $C_{2-4}$-containing hydrocarbon linker, heterocyclo (incorporating the N of Formula I), biheterocyclo (incorporating the N of Formula I);

$R^4$ is an organic radical, preferably —$CH_3$ or —$CH_2CH_3$; and $R^5$ is an organic radical, preferably $CH_3$ or $CH_2CH_3$, and further wherein the amine of Formula I is optionally charged (e.g., a quaternary nitrogen as a result of a $CH_3$ group being bound to the amine).

Examples of specific anticholinergic agents that are muscarinic receptor antagonists include those selected from the group consisting of oxybutynin, dicyclomine, oxyphencyclimine, flavoxate, clindium, cyclopentolate, eucatropine, glycopyrrolate, mepanzolate, methantheline, scopolamine, atropine and propantheline.

It is believed that an advantage of attaching a water-soluble, non-peptidic oligomer to, for example, the amine group of an anticholinergic agent (e.g., effectively "substituting" an alkyl group attached to an amine for a water-soluble, non-peptidic oligomer for) may result in reduction of side effects. Without wishing to be bound by theory, it is believed that—with respect to the representative anticholinergic agent oxybutynin—the frequently encountered side effect of dry mouth is caused by metabolism at the diethyl amine group. Because attaching a water-soluble, non-peptidic oligomer to this amine group is expected to prevent (and/or reduce) the formation of the dry mouth-causing metabolite, compounds of the invention having a water-soluble, non-peptidic oligomer attached at or near this location are expected to alleviate or reduce this side effect.

It is also believed that an advantage of the conjugates of the present invention is their ability to retain some degree of muscarinic receptor antagonism while not inducing clinically meaningful drowsiness. Although not wishing to be bound by theory, the extra size introduced by the oligomer—in contrast to the unconjugated "original" anticholinergic agent—reduces the ability of the compound to cross the blood-brain barrier. In this way, the antimuscarinic effects of the conjugate can act within the periphery while avoiding the central nervous system (and thereby avoid central nervous system-mediated side effects). The conjugates of the present invention may have other benefits as well.

Use of discrete oligomers (e.g., from a monodisperse or bimodal composition of oligomers, in contrast to relatively impure compositions) to form conjugates can advantageously alter certain properties associated with the corresponding small molecule drug. For instance, a conjugate of the invention, when administered by any of a number of suitable administration routes, such as parenteral, oral, transdermal, buccal, pulmonary, or nasal, exhibits reduced penetration across the blood-brain barrier. It is preferred that the conjugates exhibit slowed, minimal or effectively no crossing of the blood-brain barrier, while still crossing the gastro-intestinal (GI) walls and into the systemic circulation if oral delivery is intended. Moreover, the conjugates of the invention maintain a degree of bioactivity as well as bioavailability in their conjugated form.

With respect to the blood-brain barrier ("BBB"), this barrier restricts the transport of drugs from the blood to the brain. This barrier consists of a continuous layer of unique endothelial cells joined by tight junctions. The cerebral capillaries, which comprise more than 95% of the total surface area of the BBB, represent the principal route for the entry of most solutes and drugs into the central nervous system.

For compounds whose degree of blood-brain barrier crossing ability is not readily known, such ability can be determined using a suitable animal model. In addition, the degree of blood-brain barrier crossing can be determined using an in situ rat brain perfusion ("RBP") model as described herein. Briefly, the RBP technique involves cannulation of the carotid artery followed by perfusion with a compound solution under controlled conditions, followed by a wash out phase to remove compound remaining in the vascular space. (Such analyses can be conducted, for example, by contract research organizations such as Absorption Systems, Exton, Pa.). More specifically, in the RBP model, a cannula is placed in the left carotid artery and the side branches are tied off. A physiologic buffer containing the compound (5 micromolar) is perfused at a flow rate of 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl, P., et al., *J. Med. Chem.* 2000, 43, 3714-3717; and Kelder, J., et al., *Pharm. Res.* 1999, 16, 1514-1519.

With respect to the blood-brain barrier, the water-soluble oligomer-small molecule drug conjugate exhibits a blood-brain barrier crossing rate that is reduced as compared to the crossing rate of the small molecule drug not attached to the water-soluble oligomer. Exemplary reductions in blood-brain barrier crossing rates for the conjugates described herein include reductions of: at least about 5%; at least about 10%; at least about 25%; at least about 30%; at least about 40%; at least about 50%; at least about 60%; at least about 70%; at least about 80%; or at least about 90%, when compared to the blood-brain barrier crossing rate of the small molecule drug not attached to the water-soluble oligomer. A preferred reduction in the blood-brain barrier crossing rate for a conjugate is at least about 20%.

As indicated above, the compounds of the invention include a residue of an anticholinergic agent. Assays for determining whether a given compound (regardless of whether the compound is in conjugated form or not) can block muscarinic receptors are described infra.

In some instances, anticholinergic agents can be obtained from commercial sources. In addition, anticholinergic agents can be obtained through chemical synthesis. Synthetic approaches for preparing anticholinergic agents are described in the literature.

Each of these (and other) anticholinergic agents can be covalently attached (either directly or through one or more atoms) to a water-soluble, non-peptidic oligomer.

The anticholingeric agent is a small molecule drug and generally has a molecular weight of less than 1000 Da. Exemplary molecular weights of small molecule drugs include molecular weights of: less than about 950; less than about 900; less than about 850; less than about 800; less than about 750; less than about 700; less than about 650; less than about 600; less than about 550; less than about 500; less than about 450; less than about 400; less than about 350; and less than about 300.

Small molecule drugs, for the purpose of the invention, include oligopeptides, oligonucleotides, and other biomolecules having a molecular weight of less than about 1000

Daltons. Also encompassed in the term "small molecule drug" is any fragment of a peptide, protein or antibody, including native sequences and variants falling within the molecular weight range stated above. In one or more embodiments, however, it is preferred that the small molecule drug satisfies one or more of the following: not an oligopeptide; not an oligonucleotide; not an antibody; and not a fragment of any of the foregoing.

The small molecule drug used in the invention, if chiral, may be in a racemic mixture, or an optically active form, for example, a single optically active enantiomer, or any combination or ratio of enantiomers (i.e., scalemic mixture). In addition, the small molecule drug may possess one or more geometric isomers. With respect to geometric isomers, a composition can comprise a single geometric isomer or a mixture of two or more geometric isomers. A small molecule drug for use in the present invention can be in its customary active form, or may possess some degree of modification. For example, a small molecule drug may have a targeting agent, tag, or transporter attached thereto, prior to or after covalent attachment of an oligomer. Alternatively, the small molecule drug may possess a lipophilic moiety attached thereto, such as a phospholipid (e.g., distearoylphosphatidylethanolamine or "DSPE," dipalmitoylphosphatidylethanolamine or "DPPE," and so forth) or a small fatty acid. In some instances, however, it is preferred that the small molecule drug moiety does not include attachment to a lipophilic moiety.

The anticholinergic agent for coupling to a water-soluble, non-peptidic oligomer possesses a free hydroxyl, carboxyl, thio, amino group, or the like (i.e., "handle") suitable for covalent attachment to the oligomer. In addition, the anticholinergic agent can be modified by introduction of a reactive group, preferably by conversion of one of its existing functional groups to a functional group suitable for formation of a covalent linkage between the oligomer and the drug.

Accordingly, each oligomer is composed of up to three different monomer types selected from the group consisting of: alkylene oxide, such as ethylene oxide or propylene oxide; olefinic alcohol, such as vinyl alcohol, 1-propenol or 2-propenol; vinyl pyrrolidone; hydroxyalkyl methacrylamide or hydroxyalkyl methacrylate, where alkyl is preferably methyl; $\alpha$-hydroxy acid, such as lactic acid or glycolic acid; phosphazene, oxazoline, amino acids, carbohydrates such as monosaccharides, saccharide or mannitol; and N-acryloylmorpholine. Preferred monomer types include alkylene oxide, olefinic alcohol, hydroxyalkyl methacrylamide or methacrylate, N-acryloylmorpholine, and $\alpha$-hydroxy acid. Preferably, each oligomer is, independently, a co-oligomer of two monomer types selected from this group, or, more preferably, is a homo-oligomer of one monomer type selected from this group.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The two monomer types in a co-oligomer may be of the same monomer type, for example, two alkylene oxides, such as ethylene oxide and propylene oxide. Preferably, the oligomer is a homo-oligomer of ethylene oxide. Usually, although not necessarily, the terminus (or termini) of the oligomer that is not covalently attached to a small molecule is capped to render it unreactive. Alternatively, the terminus may include a reactive group. When the terminus is a reactive group, the reactive group is either selected such that it is unreactive under the conditions of formation of the final oligomer or during covalent attachment of the oligomer to a small molecule drug, or it is protected as necessary. One common end-functional group is hydroxyl or —OH, particularly for oligoethylene oxides.

The water-soluble, non-peptidic oligomer (e.g., "POLY" in various structures provided herein) can have any of a number of different geometries. For example, it can be linear, branched, or forked. Most typically, the water-soluble, non-peptidic oligomer is linear or is branched, for example, having one branch point. Although much of the discussion herein is focused upon poly(ethylene oxide) as an illustrative oligomer, the discussion and structures presented herein can be readily extended to encompass any of the water-soluble, non-peptidic oligomers described above.

The molecular weight of the water-soluble, non-peptidic oligomer, excluding the linker portion, is generally relatively low. Exemplary values of the molecular weight of the water-soluble polymer include: below about 1500; below about 1450; below about 1400; below about 1350; below about 1300; below about 1250; below about 1200; below about 1150; below about 1100; below about 1050; below about 1000; below about 950; below about 900; below about 850; below about 800; below about 750; below about 700; below about 650; below about 600; below about 550; below about 500; below about 450; below about 400; below about 350; below about 300; below about 250; below about 200; and below about 100 Daltons.

Exemplary ranges of molecular weights of the water-soluble, non-peptidic oligomer (excluding the linker) include: from about 100 to about 1400 Daltons; from about 100 to about 1200 Daltons; from about 100 to about 800 Daltons; from about 100 to about 500 Daltons; from about 100 to about 400 Daltons; from about 200 to about 500 Daltons; from about 200 to about 400 Daltons; from about 75 to 1000 Daltons; and from about 75 to about 750 Daltons.

Preferably, the number of monomers in the water-soluble, non-peptidic oligomer falls within one or more of the following ranges: between about 1 and about 30 (inclusive); between about 1 and about 25; between about 1 and about 20; between about 1 and about 15; between about 1 and about 12; between about 1 and about 10. In certain instances, the number of monomers in series in the oligomer (and the corresponding conjugate) is one of 1, 2, 3, 4, 5, 6, 7, or 8. In additional embodiments, the oligomer (and the corresponding conjugate) contains 9, 10, 11, 12, 13, 14, 15, 16, 17, 18, 19, or 20 monomers in series. In yet further embodiments, the oligomer (and the corresponding conjugate) possesses 21, 22, 23, 24, 25, 26, 27, 28, 29 or 30 monomers in series. Thus, for example, when the water-soluble, non-peptidic polymer includes $CH_3$—$(OCH_2CH_2)_n$—, "n" is an integer that can be 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30, and can fall within one or more of the following ranges: between about 1 and about 25; between about 1 and about 20; between about 1 and about 15; between about 1 and about 12; between about 1 and about 10.

When the water-soluble, non-peptidic oligomer has 1, 2, 3, 4, 5, 6, 7, 8, 9, or 10 monomers, these values correspond to a methoxy end-capped oligo(ethylene oxide) having a molecular weights of about 75, 119, 163, 207, 251, 295, 339, 383, 427, and 471 Daltons, respectively. When the oligomer has 11, 12, 13, 14, or 15 monomers, these values correspond to methoxy end-capped oligo(ethylene oxide) having molecular weights corresponding to about 515, 559, 603, 647, and 691 Daltons, respectively.

When the water-soluble, non-peptidic oligomer is attached to the anticholinergic agent (in contrast to the step-wise addition of one or more monomers to effectively "grow" the oligomer onto the anticholinergic agent), it is preferred that the composition containing an activated form of the water-soluble, non-peptidic oligomer be monodispersed. In those instances, however, where a bimodal composition is employed, the composition will possess a bimodal distribution centering around any two of the above numbers of monomers. Ideally, the polydispersity index of each peak in the bimodal distribution, Mw/Mn, is 1.01 or less, and even more preferably, is 1.001 or less, and even more preferably is 1.0005 or less. Most preferably, each peak possesses a MW/Mn value of 1.0000. For instance, a bimodal oligomer may have any one of the following exemplary combinations of monomer subunits: 1-2, 1-3, 1-4, 1-5, 1-6, 1-7, 1-8, 1-9, 1-10, and so forth; 2-3, 2-4, 2-5, 2-6, 2-7, 2-8, 2-9, 2-10, and so forth; 3-4, 3-5, 3-6, 3-7, 3-8, 3-9, 3-10, and so forth; 4-5, 4-6, 4-7, 4-8, 4-9, 4-10, and so forth; 5-6, 5-7, 5-8, 5-9, 5-10, and so forth; 6-7, 6-8, 6-9, 6-10, and so forth; 7-8, 7-9, 7-10, and so forth; and 8-9, 8-10, and so forth.

In some instances, the composition containing an activated form of the water-soluble, non-peptidic oligomer will be trimodal or even tetramodal, possessing a range of monomers units as previously described. Oligomer compositions possessing a well-defined mixture of oligomers (i.e., being bimodal, trimodal, tetramodal, and so forth) can be prepared by mixing purified monodisperse oligomers to obtain a desired profile of oligomers (a mixture of two oligomers differing only in the number of monomers is bimodal; a mixture of three oligomers differing only in the number of monomers is trimodal; a mixture of four oligomers differing only in the number of monomers is tetramodal), or alternatively, can be obtained from column chromatography of a polydisperse oligomer by recovering the "center cut", to obtain a mixture of oligomers in a desired and defined molecular weight range.

It is preferred that the water-soluble, non-peptidic oligomer is obtained from a composition that is preferably unimolecular or monodisperse. That is, the oligomers in the composition possess the same discrete molecular weight value rather than a distribution of molecular weights. Some monodisperse oligomers can be purchased from commercial sources such as those available from Sigma-Aldrich, or alternatively, can be prepared directly from commercially available starting materials such as Sigma-Aldrich. Water-soluble, non-peptidic oligomers can be prepared as described in Chen Y., Baker, G. L., J. Org. Chem., 6870-6873 (1999), WO 02/098949, and U.S. Patent Application Publication 2005/0136031.

When present, the spacer moiety (through which the water-soluble, non-peptidic polymer is attached to the anticholinergic agent) may be a single bond, a single atom, such as an oxygen atom or a sulfur atom, two atoms, or a number of atoms. A spacer moiety is typically but is not necessarily linear in nature. The spacer moiety, "X" is hydrolytically stable, and is preferably also enzymatically stable. Preferably, the spacer moiety "X" is one having a chain length of less than about 12 atoms, and preferably less than about 10 atoms, and even more preferably less than about 8 atoms and even more preferably less than about 5 atoms, whereby length is meant the number of atoms in a single chain, not counting substituents. For instance, a urea linkage such as this, $R_{oligomer}$—NH—(C=O)—NH—$R'_{drug}$, is considered to have a chain length of 3 atoms (—NH—C(O)—NH—). In selected embodiments, the linkage does not comprise further spacer groups.

In some instances, the spacer moiety "X" comprises an ether, amide, urethane, amine, thioether, urea, or a carbon-carbon bond. Functional groups such as those discussed below, and illustrated in the examples, are typically used for forming the linkages. The spacer moiety may less preferably also comprise (or be adjacent to or flanked by) spacer groups, as described further below. Spacers are most useful in instances where the bioactivity of the conjugate is significantly reduced due to the positioning of the oligomer on the parent drug.

More specifically, in selected embodiments, a spacer moiety, X, may be any of the following: "—" (i.e., a covalent bond, that may be stable or degradable, between the residue of the small molecule anticholinergic agent and the water-soluble, non-peptidic oligomer), —O—, —NH—, —S—, —C(O)—, C(O)—NH, NH—C(O)—NH, O—C(O)—NH, —C(S)—, —$CH_2$—, —$CH_2$—$CH_2$—, —$CH_2$—$CH_2$—$CH_2$—, —$CH_2$—$CH_2$—$CH_2$—$CH_2$—, —O—$CH_2$—, —$CH_2$—O—, —O—$CH_2$—$CH_2$—, —$CH_2$—O—$CH_2$—, —$CH_2$—$CH_2$—O—, —O—$CH_2$—$CH_2$—$CH_2$—, —$CH_2$—O—$CH_2$—$CH_2$—, —$CH_2$—$CH_2$—O—$CH_2$—, —$CH_2$—$CH_2$—$CH_2$—O—, —O—$CH_2$—$CH_2$—$CH_2$—$CH_2$—, —$CH_2$—O—$CH_2$—$CH_2$—$CH_2$—, —$CH_2$—$CH_2$—O—$CH_2$—$CH_2$—, —$CH_2$—$CH_2$—$CH_2$—O—$CH_2$—, —$CH_2$—$CH_2$—$CH_2$—$CH_2$—O—, —C(O)—NH—$CH_2$—, —C(O)—NH—$CH_2$—$CH_2$—, —$CH_2$—C(O)—NH—$CH_2$—, —$CH_2$—$CH_2$—C(O)—NH—, —C(O)—NH—$CH_2$—$CH_2$—$CH_2$—, —$CH_2$—C(O)—NH—$CH_2$—$CH_2$—, —$CH_2$—$CH_2$—C(O)—NH—$CH_2$—, —$CH_2$—$CH_2$—$CH_2$—C(O)—NH—, —C(O)—NH—$CH_2$—$CH_2$—$CH_2$—$CH_2$—, —$CH_2$—C(O)—NH—$CH_2$—$CH_2$—$CH_2$—, —$CH_2$—$CH_2$—C(O)—NH—$CH_2$—$CH_2$—, —$CH_2$—$CH_2$—$CH_2$—C(O)—NH—$CH_2$—, —$CH_2$—$CH_2$—$CH_2$—C(O)—NH—$CH_2$—$CH_2$—, —$CH_2$—$CH_2$—$CH_2$—$CH_2$—C(O)—NH—NH—C(O)—$CH_2$—, —$CH_2$—NH—C(O)—$CH_2$—, —$CH_2$—$CH_2$—NH—C(O)—$CH_2$—, —NH—C(O)—$CH_2$—$CH_2$—, —$CH_2$—NH—C(O)—$CH_2$—$CH_2$, —$CH_2$—$CH_2$—NH—C(O)—$CH_2$—$CH_2$, —C(O)—NH—$CH_2$—, —C(O)—NH—$CH_2$—$CH_2$—, —O—C(O)—NH—$CH_2$—, —O—C(O)—NH—$CH_2$—$CH_2$—, —NH—$CH_2$—, —NH—$CH_2$—$CH_2$—, —$CH_2$—NH—$CH_2$—, —$CH_2$—$CH_2$—NH—$CH_2$—, —C(O)—$CH_2$—, —C(O)—$CH_2$—$CH_2$—, —$CH_2$—C(O)—$CH_2$—, —$CH_2$—$CH_2$—C(O)—$CH_2$—, —$CH_2$—$CH_2$—C(O)—$CH_2$—$CH_2$—, —$CH_2$—$CH_2$—C(O)—, —$CH_2$—$CH_2$—$CH_2$—C(O)—NH—$CH_2$—$CH_2$—NH—, —$CH_2$—$CH_2$—$CH_2$—C(O)—NH—$CH_2$—$CH_2$—NH—C(O)—, —$CH_2$—$CH_2$—$CH_2$—C(O)—NH—$CH_2$—$CH_2$—NH—C(O)—$CH_2$—, bivalent cycloalkyl group, —N($R^6$)—, $R^6$ is H or an organic radical selected from the group consisting of alkyl, substituted alkyl, alkenyl, substituted alkenyl, alkynyl, substituted alkynyl, aryl and substituted aryl.

For purposes of the present invention, however, a series of atoms is not considered as a spacer moiety when the series of atoms is immediately adjacent to an oligomer segment, and the series of atoms is but another monomer such that the proposed linkage would represent a mere extension of the oligomer chain.

The spacer moiety "X" between the water-soluble, non-peptidic oligomer and the small molecule is typically formed by reaction of a functional group on a terminus of the oligomer (or one or more monomers when it is desired to "grow"

the oligomer onto the anticholinergic agent) with a corresponding functional group within the anticholinergic agent. Illustrative reactions are described briefly below. For example, an amino group on an oligomer may be reacted with a carboxylic acid or an activated carboxylic acid derivative on the small molecule, or vice versa, to produce an amide linkage. Alternatively, reaction of an amine on an oligomer with an activated carbonate (e.g. succinimidyl or benzotriazyl carbonate) on the drug, or vice versa, forms a carbamate linkage. Reaction of an amine on an oligomer with an isocyanate (R—N=C=O) on a drug, or vice versa, forms a urea linkage (R—NH—(C=O)—NH—R'). Further, reaction of an alcohol (alkoxide) group on an oligomer with an alkyl halide, or halide group within a drug, or vice versa, forms an ether linkage. In yet another coupling approach, a small molecule having an aldehyde function is coupled to an oligomer amino group by reductive amination, resulting in formation of a secondary amine linkage between the oligomer and the small molecule.

A particularly preferred water-soluble, non-peptidic oligomer is an oligomer bearing an aldehyde functional group. In this regard, the oligomer will have the following structure: $CH_3O$—$(CH_2$—$CH_2$—$O)_n$—$(CH_2)_p$—$C(O)H$, wherein (n) is one of 1, 2, 3, 4, 5, 6, 7, 8, 9 and 10 and (p) is one of 1, 2, 3, 4, 5, 6 and 7. Preferred (n) values include 3, 5 and 7 and preferred (p) values 2, 3 and 4. In addition, the carbon atom alpha to the —C(O)H moiety can optionally be substituted with alkyl.

Typically, the terminus of the water-soluble, non-peptidic oligomer not bearing a functional group is capped to render it unreactive. When the oligomer does include a further functional group at a terminus other than that intended for formation of a conjugate, that group is either selected such that it is unreactive under the conditions of formation of the spacer moiety "X," or it is protected during the formation of the spacer moiety "X."

As stated above, the water-soluble, non-peptidic oligomer includes at least one functional group prior to conjugation. The functional group typically comprises an electrophilic or nucleophilic group for covalent attachment to a small molecule, depending upon the reactive group contained within or introduced into the small molecule. Examples of nucleophilic groups that may be present in either the oligomer or the small molecule include hydroxyl, amine, hydrazine (—$NHNH_2$), hydrazide (—$C(O)NHNH_2$), and thiol. Preferred nucleophiles include amine, hydrazine, hydrazide, and thiol, particularly amine. Most small molecule drugs for covalent attachment to an oligomer will possess a free hydroxyl, amino, thio, aldehyde, ketone, or carboxyl group.

Examples of electrophilic functional groups that may be present in either the oligomer or the small molecule include carboxylic acid, carboxylic ester, particularly imide esters, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, and halosilane. More specific examples of these groups include succinimidyl ester or carbonate, imidazoyl ester or carbonate, benzotriazole ester or carbonate, vinyl sulfone, chloroethylsulfone, vinylpyridine, pyridyl disulfide, iodoacetamide, glyoxal, dione, mesylate, tosylate, and tresylate (2,2,2-trifluoroethanesulfonate).

Also included are sulfur analogs of several of these groups, such as thione, thione hydrate, thioketal, is 2-thiazolidine thione, etc., as well as hydrates or protected derivatives of any of the above moieties (e.g. aldehyde hydrate, hemiacetal, acetal, ketone hydrate, hemiketal, ketal, thioketal, thioacetal).

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include imide esters, of the general form —(CO)O—N[(CO)—]$_2$; for example, N-hydroxysuccinimidyl (NHS) esters or N-hydroxyphthalimidyl esters. Also preferred are imidazolyl esters and benzotriazole esters. Particularly preferred are activated propionic acid or butanoic acid esters, as described in co-owned U.S. Pat. No. 5,672,662. These include groups of the form —$(CH_2)_{2-3}$C(=O)O-Q, where Q is preferably selected from N-succinimide, N-sulfosuccinimide, N-phthalimide, N-glutarimide, N-tetrahydrophthalimide, N-norbornene-2,3-dicarboximide, benzotriazole, 7-azabenzotriazole, and imidazole.

Other preferred electrophilic groups include succinimidyl carbonate, maleimide, benzotriazole carbonate, glycidyl ether, imidazoyl carbonate, p-nitrophenyl carbonate, acrylate, tresylate, aldehyde, and orthopyridyl disulfide.

These electrophilic groups are subject to reaction with nucleophiles, e.g. hydroxy, thio, or amino groups, to produce various bond types. Preferred for the present invention are reactions which favor formation of a hydrolytically stable linkage. For example, carboxylic acids and activated derivatives thereof, which include orthoesters, succinimidyl esters, imidazolyl esters, and benzotriazole esters, react with the above types of nucleophiles to form esters, thioesters, and amides, respectively, of which amides are the most hydrolytically stable. Carbonates, including succinimidyl, imidazolyl, and benzotriazole carbonates, react with amino groups to form carbamates. Isocyanates (R—N=C=O) react with hydroxyl or amino groups to form, respectively, carbamate (RNH—C(O)—OR') or urea (RNH—C(O)—NHR') linkages. Aldehydes, ketones, glyoxals, diones and their hydrates or alcohol adducts (i.e. aldehyde hydrate, hemiacetal, acetal, ketone hydrate, hemiketal, and ketal) are preferably reacted with amines, followed by reduction of the resulting imine, if desired, to provide an amine linkage (reductive amination).

Several of the electrophilic functional groups include electrophilic double bonds to which nucleophilic groups, such as thiols, can be added, to form, for example, thioether bonds. These groups include maleimides, vinyl sulfones, vinyl pyridine, acrylates, methacrylates, and acrylamides. Other groups comprise leaving groups that can be displaced by a nucleophile; these include chloroethyl sulfone, pyridyl disulfides (which include a cleavable S—S bond), iodoacetamide, mesylate, tosylate, thiosulfonate, and tresylate. Epoxides react by ring opening by a nucleophile, to form, for example, an ether or amine bond. Reactions involving complementary reactive groups such as those noted above on the oligomer and the small molecule are utilized to prepare the conjugates of the invention.

In some instances the anticholinergic agent may not have a functional group suited for conjugation. In this instance, it is possible to modify the "original" anticholinergic agent so that it does have the desired anticholinergic agent. For example, if the anticholinergic agent has an amide group, but an amine group is desired, it is possible to modify the amide group to an amine group by way of a Hofmann rearrangement, Curtius rearrangement (once the amide is converted to an azide) or Lossen rearrangement (once the amide is concerted to hydroxamide followed by treatment with tolyene-2-sulfonyl chloride/base).

It is possible to prepare a conjugate of small molecule anticholinergic agent bearing a carboxyl group wherein the carboxyl group-bearing small molecule anticholinergic agent is coupled to an amino-terminated oligomeric ethylene glycol, to provide a conjugate having an amide group covalently linking the small molecule anticholinergic agent to the oligomer. This can be performed, for example, by combining the carboxyl group-bearing small molecule anticholinergic agent with the amino-terminated oligomeric ethylene glycol in the presence of a coupling reagent, (such as dicyclohexylcarbodiimide or "DCC") in an anhydrous organic solvent.

Further, it is possible to prepare a conjugate of a small molecule anticholinergic agent bearing a hydroxyl group wherein the hydroxyl group-bearing small molecule anticholinergic agent is coupled to an oligomeric ethylene glycol halide to result in an ether (—O—) linked small molecule conjugate. This can be performed, for example, by using sodium hydride to deprotonate the hydroxyl group followed by reaction with a halide-terminated oligomeric ethylene glycol.

In another example, it is possible to prepare a conjugate of a small molecule anticholinergic agent bearing a ketone group by first reducing the ketone group to form the corresponding hydroxyl group. Thereafter, the small molecule anticholinergic agent now bearing a hydroxyl group can be coupled as described herein.

In still another instance, it is possible to prepare a conjugate of a small molecule anticholinergic agent bearing an amine group. In one approach, the amine group-bearing small molecule anticholinergic agent and an aldehyde-bearing oligomer are dissolved in a suitable buffer after which a suitable reducing agent (e.g., $NaCNBH_3$) is added. Following reduction, the result is an amine linkage formed between the amine group of the amine group-containing small molecule anticholinergic agent and the carbonyl carbon of the aldehyde-bearing oligomer.

In another approach for preparing a conjugate of a small molecule anticholinergic agent bearing an amine group, a carboxylic acid-bearing oligomer and the amine group-bearing small molecule anticholinergic agent are combined, typically in the presence of a coupling reagent (e.g., DCC). The result is an amide linkage formed between the amine group of the amine group-containing small molecule anticholinergic agent and the carbonyl of the carboxylic acid-bearing oligomer.

Exemplary conjugates of the anticholinergic agents of Formula I include those having the following structure:

Formula I-Ca wherein each of $R^1$, $R^2$, $R^3$, $L^2$, $R^5$, and the optional quaternary amine is as previously defined with respect to Formula I, and X is a spacer moiety, and POLY is a water-soluble, non-peptidic oligomer. With respect to Formula I-Ca, preferred "POLY" include $(CH_2CH_2O)_nCH_3$, wherein (n) is 1 to 20. Also with respect to Formula I-Ca, a preferred X is a stable covalent linkage (i.e., "—")

Further exemplary conjugates of the anticholinergic agents include those having the following structure:

Formula I-Cb 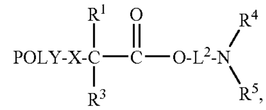 wherein each of $R^1$, $R^2$, $R^3$, L, $R^5$, and the optional quaternary amine is as previously defined with respect to Formula I, and X is a spacer moiety, and POLY is a water-soluble, non-peptidic oligomer. With respect to Formula I-Cb, preferred "POLY" include $(CH_2CH_2O)_nCH_3$, wherein (n) is 1 to 20. Also with respect to Formula I-Cb, a preferred X is a stable covalent linkage (i.e., "—")

The conjugates of the invention can exhibit a reduced blood-brain barrier crossing rate. Moreover, the conjugates maintain at least about 5%, 10%, 20%, 30%, 40%, 50%, 60%, 70%, or more of the bioactivity of the unmodified parent small molecule drug.

The selection of an optimally sized oligomer can be determined as follows.

First, an oligomer obtained from a monodisperse or bimodal water soluble oligomer is conjugated to the small molecule drug. Preferably, the drug is orally bioavailable, and on its own, exhibits a blood-brain barrier crossing rate. Next, the ability of the conjugate to cross the blood-brain barrier is determined using an appropriate model and compared to that of the unmodified parent drug. If the results are favorable, that is to say, if, for example, the rate of crossing is significantly reduced, then the bioactivity of conjugate is further evaluated. In one or more embodiments, the drug in conjugated form can be bioactive, and preferably, maintains a significant degree of bioactivity relative to the parent drug, i.e., greater than about 30% of the bioactivity of the parent drug, or even more preferably, greater than about 50% of the bioactivity of the parent drug.

Then, the above steps are repeated using oligomers of the same monomer type but having a different number of subunits.

For each conjugate whose ability to cross the blood-brain barrier is reduced in comparison to the non-conjugated small molecule drug, its oral bioavailability is then assessed. Based upon these results, that is to say, based upon the sequential addition of increasing numbers of discrete monomers to a given small molecule at a given position or location within the small molecule, it is possible to determine the size of the oligomer most effective in providing a conjugate having an optimal balance between reduction in biological membrane crossing, oral bioavailability, and bioactivity. The small size of the oligomers makes such screenings feasible, and allows one to effectively tailor the properties of the resulting conjugate. By making small, incremental changes in oligomer size, and utilizing an experimental design approach, one can effectively identify a conjugate having a favorable balance of reduction in biological membrane crossing rate, bioactivity, and oral bioavailability. In some instances, attachment of an oligomer as described herein is effective to actually increase oral bioavailability of the drug.

For example, one of ordinary skill in the art, using routine experimentation, can determine a best suited molecular size and linkage for improving oral bioavailability by first preparing a series of oligomers with different weights and functional groups and then obtaining the necessary clearance profiles by administering the conjugates to a patient and taking periodic blood and/or urine sampling. Once a series of clearance profiles have been obtained for each tested conjugate, a suitable conjugate can be identified.

Animal models (e.g., rodents and dogs) can also be used to study oral drug transport. In addition, non-in vivo methods include rodent everted gut excised tissue and Caco-2 cell monolayer tissue-culture models. In addition, the Experimental provides additional approaches to test oral drug transport. These models are useful in predicting oral drug bioavailability.

To determine whether the anticholinergic agent of Formula I or the conjugate of an anticholinergic agent and a water-soluble, non-peptidic polymer has binding activity to muscarinic receptors and/or has antimuscarinic receptor antagonist activity to, it is possible to test such a compound. For example, the muscarinic receptor affinity can be determined by an in vitro receptor binding assay which utilizes a cell membrane preparation from the Chinese hamster ovary cells expressing the recombinant human muscarinic receptors. Briefly, in a radioligand binding study, the inhibitory activity of a compound can be determined using a modification of the method described in Hegde et al. (1997) Br. J. Pharmacol., 120:1409-1418. In this approach, cell membranes from Chinese hamster ovary cells expressing the recombinant human muscarinic receptors can be used. The assays are conducted with the radioligand [$^3$H]N-methyl scopolamine (0.4 nM, specific activity 84 Ci/mmol$^{-1}$) in a final volume of 0.25 mL Tris-Krebs buffer. Non-specific binding is defined with 1 μM atropine.

In another test, it is possible to determine the inhibition of volume-induced contractions in rats. Briefly, the muscarinic receptor inhibitory activity in vivo can be determined in rats using a modification of the method described in Hegde et al. (1996) Proceedings of the 26th Annual Meeting of the International Continence Society (August 27th 30th), Abstract 126. Female Sprague-Dawley rats can be anesthetized with urethane and instrumented for intravenous administration of drugs and, in some cases, measurement of arterial pressure, heart rate and intra-bladder pressure. The effect of test compounds on volume-induced bladder contractions can be determined in separate groups of animals. Volume-induced reflex bladder contractions can be induced by filling the bladder with saline. The test compound can be administered intravenously in a cumulative manner at 10-minute intervals. Atropine (0.3 mg/kg, iv) can be administered at the end of the study as a positive control.

The present invention also includes pharmaceutical preparations comprising a conjugate as provided herein in combination with a pharmaceutical excipient. Generally, the conjugate itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate in the composition will vary depending on a number of factors, but will optimally be a therapeutically effective dose when the composition is stored in a unit dose container. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5%-98% by weight, more preferably from about 15-95% by weight of the excipient, with concentrations less than 30% by weight most preferred.

These foregoing pharmaceutical excipients along with other excipients and general teaching regarding pharmaceutical preparations are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

The pharmaceutical compositions can take any number of forms and the invention is not limited in this regard. Exemplary preparations are most preferably in a form suitable for oral administration such as a tablet, caplet, capsule, gel cap, troche, dispersion, suspension, solution, elixir, syrup, lozenge, transdermal patch, spray, suppository, and powder.

Oral dosage forms are preferred for those conjugates that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the conjugates described herein. In addition to the conjugate, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the conjugate-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The conjugate can also be administered through the skin using conventional transdermal patch or other transdermal delivery system, wherein the conjugate is contained within a laminated structure that serves as a drug delivery device to be affixed to the skin. In such a structure, the conjugate is contained in a layer, or "reservoir," underlying an upper backing layer. The laminated structure can contain a single reservoir, or it can contain multiple reservoirs.

The conjugate can also be formulated into a suppository for rectal administration. With respect to suppositories, the conjugate is mixed with a suppository base material which is (e.g., an excipient that remains solid at room temperature but softens, melts or dissolves at body temperature) such as coca butter (theobroma oil), polyethylene glycols, glycerinated gelatin, fatty acids, and combinations thereof. Suppositories can be prepared by, for example, performing the following steps (not necessarily in the order presented): melting the suppository base material to form a melt; incorporating the conjugate (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a conjugate as provided herein to a patient suffering from a condition that is responsive to treatment with the conjugate. The method comprises administering, generally orally, a therapeutically effective amount of the conjugate (preferably provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

In instances where parenteral administration is utilized, it may be necessary to employ somewhat bigger oligomers than those described previously, with molecular weights ranging from about 500 to 30K Daltons (e.g., having molecular weights of about 500, 1000, 2000, 2500, 3000, 5000, 7500, 10000, 15000, 20000, 25000, 30000 or even more).

The method of administering may be used to treat any condition that can be remedied or prevented by administration of the particular conjugate. Those of ordinary skill in the art appreciate which conditions a specific conjugate can effectively treat. The actual dose to be administered will vary depend upon the age, weight, and general condition of the subject as well as the severity of the condition being treated, the judgment of the health care professional, and conjugate being administered. Therapeutically effective amounts are known to those skilled in the art and/or are described in the pertinent reference texts and literature. Generally, a therapeutically effective amount will range from about 0.001 mg to 1000 mg, preferably in doses from 0.01 mg/day to 750 mg/day, and more preferably in doses from 0.10 mg/day to 500 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are incorporated by reference in their entireties. In the event of an inconsistency between the teachings of this specification and the art incorporated by reference, the meaning of the teachings in this specification shall prevail.

EXPERIMENTAL

It is to be understood that while the invention has been described in conjunction with certain preferred and specific embodiments, the foregoing description as well as the examples that follow are intended to illustrate and not limit the scope of the invention. Other aspects, advantages and modifications within the scope of the invention will be apparent to those skilled in the art to which the invention pertains All chemical reagents referred to in the appended examples are commercially available unless otherwise indicated. The preparation of PEG-mers is described in, for example, U.S. Patent Application Publication No. 2005/0136031.

All $^1$H NMR (nuclear magnetic resonance) data was generated by a NMR spectrometer manufactured by Bruker (MHz≧300).

Synthesis of PEG-Oxybutynin

PEG-Oxybutynin was prepared. Schematically, the approach followed for this example is shown below.

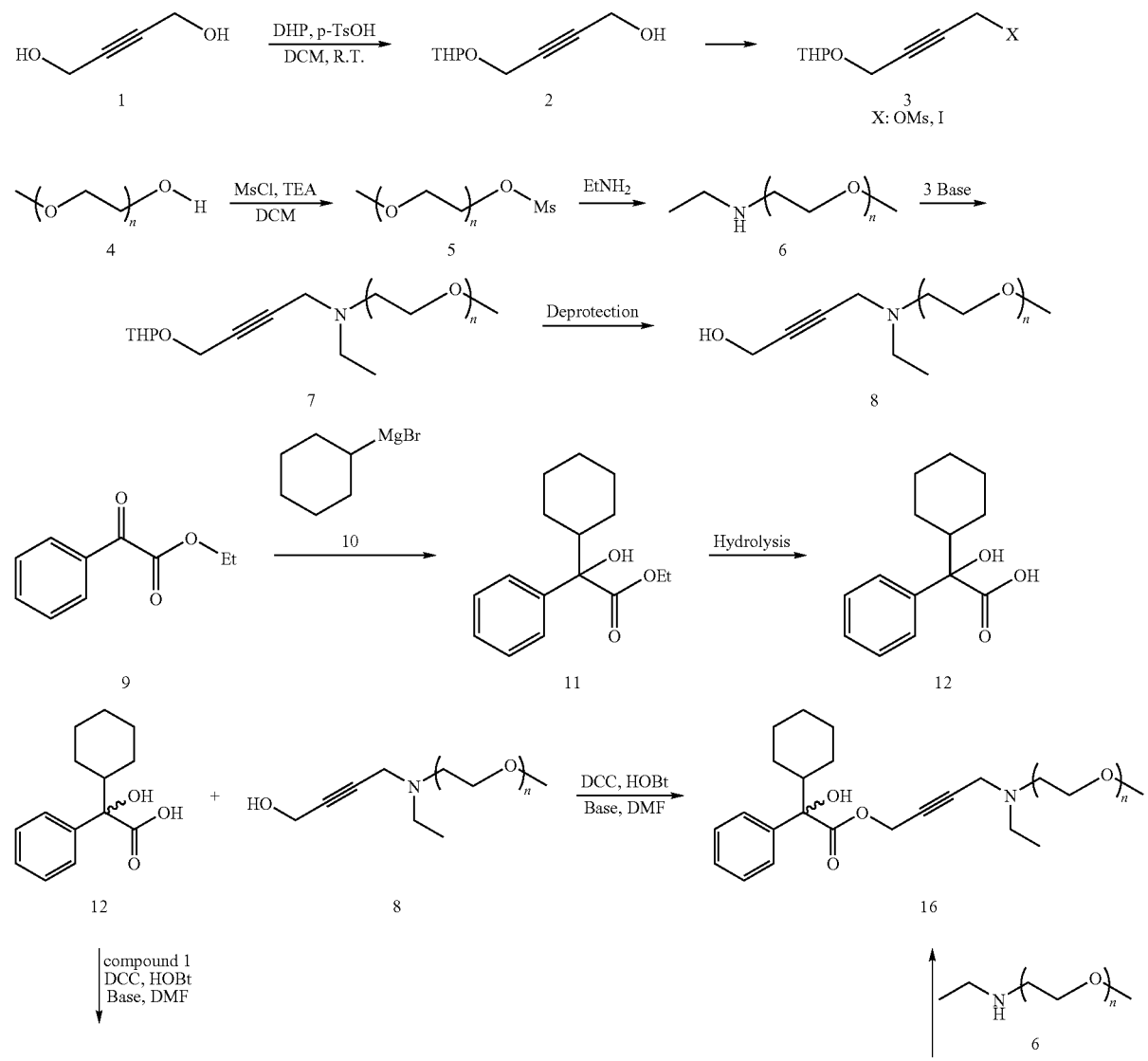

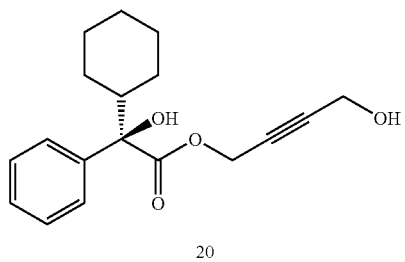

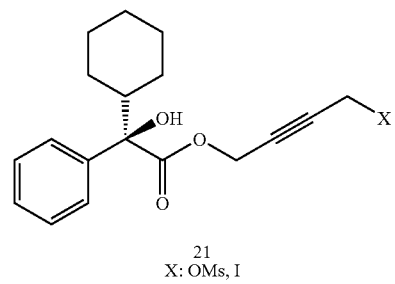

X: OMs, I

Synthesis of 4-(tetrahydro-pyran-2-yloxy)-but-2-yn-1-ol (2)

3,4-Dihydro-2H-pyron (18.3 mL, 0.196 mol) in dichloromethane (30 mL) was added dropwise over 30 minutes to a stirred solution of 2-butyne-1,4-di-ol (16.832 g, 0.194 mol) and p-TsOH (2.236 g, 11.58 mmol) in DCM (250 mL) at 0° C. After addition, the mixture was stirred at room temperature for 4 hours. Sodium bicarbonate (858 mg) was added. The mixture was stirred for another hour. Water (10 mL) was added, followed by addition of saturated aqueous potassium carbonate (150 mL). The organic phase was separated and washed with brine (200 mL), dried over anhydrous sodium sulfate, and concentrated under reduced pressure (temperature below 25° C.). The residue was separated by flash column chromatography on silica gel using 5-25% EtOAc/hexane to afford 12.88 g of product (yield: 39%), along with 12.05 g of di-protected side product. $^1$H-NMR (CDCl$_3$): δ 4.78 (t, J=3.0-3.3 Hz, 1 H), 4.37-4.21 (m, 4 H), 3.86-3.78 (m, 1 H), 3.55-3.50 (m, 1 H), 1.83-1.64 (m, 6 H).

Synthesis of 4-(tetrahydro-pyran-2-yloxy)-but-2-ynyl mesylate (3) (x=Ms)

Methanesulfonyl chloride (1.0 mL, 12.80 mmol) was added dropwise to a stirred solution of 4-(tetrahydro-pyran-2-yloxy)-but-2-yn-1-ol (1.9232 g, 11.30 mmol) and TEA (2.5 mL, 17.85 mmol) in DCM (40 mL) at ° C. for five minutes. And then the resulting mixture was stirred at room temperature for 5.5 hours. Water (20 mL) was added, followed by addition of saturated aqueous NaCl solution (70 mL). The organic phase was separated and washed again with brine (60 mL), dried over Na$_2$SO$_4$, concentrated. The residue was separated by flash column chromatography on silica gel using 5-25% EtOAc/hexane to afford 1.542 g of product (yield 55%, oil), along with 400 mg of Di-4-(tetrahydro-pyran-2-yloxy)-but-2-ynyl ether (yield 22%). $^1$H-NMR (CDCl$_3$): δ 4.88 (t, J=1.8 Hz, 2 H), 4.76 (t, J=3.0-3.3 Hz, 1 H), 4.37-4.24 (m, 2 H), 3.80-3.76 (m, 1 H), 3.54-3.50 (m, 1 H), 3.11 (s, 3 H), 1.78-1.51 (m, 6 H).

Synthesis of 4-(tetrahydro-pyran-2-yloxy)-but-2-ynyl iodide (3) (x=I)

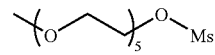

To a stirred solution of triphenylphosphine (1.4154 g, 5.34 mmol) in anhydrous dichlormethane (20 mL) at room temperature under nitrogen was added imidazole (360 mg, 5.24 mmol), followed by iodide (1.2688 g, 4.95 mmol). The mixture was stirred for three minutes, a solution of 4-(tetrahydro-pyran-2-yloxy)-but-2-yn-1-ol (708.6 mg, 4.16 mmol) in dichloromethane was added dropwise via spring. The resulting mixture was continued to be stirred for 1.5 hours. The mixture was filtered through a pad of Celite. And the solid was washed with dichloromethane. The combined organic filtration was concentrated under reduced pressure. The residue was separated with flash column chromatography on silica using 0-20% EtOAc/hexane to afford 654 mg of product in 56% yield. $^1$H-NMR (CDCl$_3$): δ 4.77 (t, J=3.0 Hz, 1 H), 4.33-4.18 (m, 2 H), 3.85-3.77 (m, 1 H), 3.70 (t, J=2.1 Hz, 2 H), 3.56-3.49 (m, 1 H), 1.85-1.62 (m, 6 H).

Synthesis of mPEG$_5$-OMs (5) (n=5)

MsCl (2.5 mL, 32 mmol) was added dropwise to a stirred solution of mPEG$_5$-OH (5.30 g, 21 mmol) and TEA (6 mL, 42.8 mmol) in dichloromethane (50 mL) at 0° C. After addition, the resulting solution was stirred at room temperature for 22 hours. Water (10 mL) was added to quench the reaction and some saturated NaCl solution (~40 mL) was added. The organic solution was separated and washed with brine (2×45 mL), dried over Na$_2$SO$_4$, and concentrated. The residue was dried under high vacuum to afford the product as a oil in quantitative yield. $^1$H-NMR (CDCl$_3$): δ 4.38-4.35 (m, 2 H), 3.76-3.73 (m, 2 H), 3.66-3.60 (m, 14 H), 3.55-3.51 (m, 2 H), 3.36 (s, 3 H), 3.06 (s, 3 H).

Other mPEG$_n$-OMs (n=3, 4, 6-20) was and/or can be synthesized following the same procedures from the corresponding mPEG$_n$-OH.

Synthesis of mPEG$_4$-NHEt (6) (n=4)

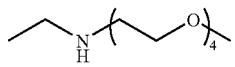

Ethylamine (70 wt % solution in water) (8 mL, 98.9 mmol) was added to a stirred solution of mPEG$_4$-OMs (2.75 g, 9.6 mmol) and K$_2$CO$_3$ (6.72 g, 48.16 mmol) in water (10 mL) at 0° C. Tetrabutylammonium bromide (268 mg, 0.82 mmol) was added. The resulting mixture was stirred at room temperature for 67 hours. The mixture was extracted with dichloromethane (3×20 mL). The combined organic solution was washed with brine, dried over anhydrous Na$_2$SO$_4$, concentrated to afford the product (2.373 g, 90.6% purity based on $^1$H-NMR) in 95% yield. $^1$H-NMR (CDCl$_3$): δ 3.64-3.51 (m, 14 H), 3.36 (s, 3 H), 2.76 (t, J=5.1-5.4 Hz, 2 H), 2.63 (q, J=7.2 H, 2 H), 1.09 (t, J=7.2 Hz, 3 H).

Other mPEG$_n$-NHEt can be synthesized following the same procedures from the corresponding mPEG$_n$-OMs.

Synthesis of ethyl-mPEG$_3$-4-(tetrahydropyran-2-yloxy)-but-2-ynyl]amine (7) (n=3)

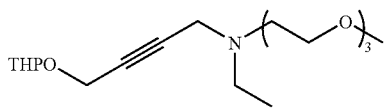

A mixture of 4-(tetrahydro-pyran-2-yloxy)-but-2-ynyl iodide (153 mg, 0.55 mmol), mPEG$_3$-NHEt (124 mg, 0.58 mmol, 90% pure) in THF (3 mL) in the presence of sodium bicarbonate (131 mg, 1.56 mmol) was stirred for 24.5 hours at room temperature. Water was added to quench the reaction. The mixture was concentrated under reduced pressure to remove the organic solvent. The remaining aqueous solution was extracted with EtOAc. The organic extraction was washed with brine, dried over sodium sulfate, concentrated. The residue was purified with flash column chromatography on silica gel using 0-9% MeOH/dichloromethane to afford the product (85 mg, 45% yield). $^1$H-NMR (CDCl$_3$): δ 4.77 (t, J=3.0 Hz, 1 H), 4.30-4.16 (m, 2 H), 3.83-3.75 (m, 1 H), 3.63-3.45 (m, 13 H), 3.33 (s, 3 H), 2.66 (t, J=6.0 Hz, 2 H), 2.53 (q, J=7.2 Hz, 2 H), 1.82-1.47 (m, 6 H), 1.01 (t, J=7.2 Hz, 3 H).

Synthesis of Ethyl-mPEG$_6$-4-(tetrahydropyran-2-yloxy)-but-2-ynyl]amine (7) (n=6)

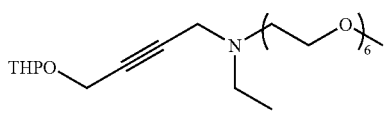

A mixture of 4-(tetrahydro-pyran-2-yloxy)-but-2-ynyl iodide (376 mg, 1.34 mmol), mPEG$_6$-NHEt (528 mg, 1.52 mmol, 93% pure) in THF (5 mL) in the presence of sodium bicarbonate (345 mg, 4.11 mmol) was stirred for 25 hours at room temperature. Water was added to quench the reaction. The mixture was concentrated under reduced pressure to remove the organic solvent. The remaining aqueous solution was mixed with saturated aqueous potassium carbonate solution (10 mL), extracted with EtOAc (3×40 mL). The combined organic solution was washed with brine, dried over sodium sulfate, concentrated. The residue was purified with flash column chromatography on silica gel using 0-9% MeOH/dichloromethane to afford the product (293 mg, 46% yield). $^1$H-NMR (CDCl$_3$): δ 4.80 (t, J=3.0 Hz, 1 H), 4.33-4.20 (m, 2 H), 3.86-3.78 (m, 1 H), 3.64-3.48 (m, 25 H), 3.36 (s, 3 H), 2.69 (t, J=6.0 Hz, 2 H), 2.56 (q, J=7.2 Hz, 2 H), 1.85-1.62 (m, 6 H), 1.04 (t, J=7.2 Hz, 3 H).

Synthesis of Ethyl-mPEG$_9$-4-(tetrahydropyran-2-yloxy)-but-2-ynyl]amine (7) (n=9)

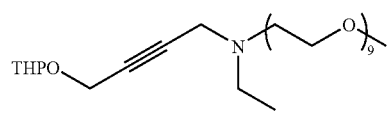

A mixture of 4-(tetrahydro-pyran-2-yloxy)-but-2-ynyl iodide (587 mg, 2.10 mmol), mPEG$_9$-NHEt (1.143 g, 2.38 mmol, 95% pure) in THF (5 mL) in the presence of sodium bicarbonate (642 mg, 7.64 mmol) was stirred for 26 hours at room temperature. Water was added to quench the reaction. The mixture was concentrated under reduced pressure to remove the organic solvent. The remaining aqueous solution was mixed with saturated aqueous potassium carbonate solution (10 mL), extracted with dichloromethane (3×20 mL). The combined organic solution was washed with brine, dried over sodium sulfate, concentrated. The residue was purified with flash column chromatography on silica gel using 0-5% MeOH/dichloromethane to afford the product (683 mg, 54% yield). $^1$H-NMR (CDCl$_3$): δ 4.80 (t, J=3.0 Hz, 1 H), 4.32-4.21 (m, 2 H), 3.83 (m, 1 H), 3.64-3.48 (m, 37 H), 3.36 (s, 3 H), 2.69 (t, J=6.0 Hz, 2 H), 2.58 (q, J=7.2 Hz, 2 H), 1.85-1.62 (m, 6 H), 1.04 (t, J=7.2 Hz, 3 H).

Synthesis of 4-(mPEG$_6$ ethylamino)-but-2-yn-1-ol (8) (n=6)

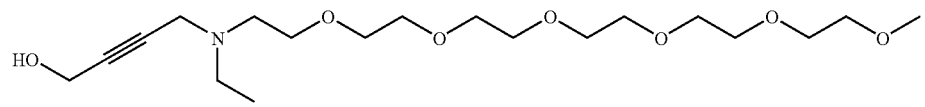 [SMILES: CCN(CC#CCO)CCOCCOCCOCCOCCOCCOC]

Ethyl-mPEG$_6$-4-(tetrahydropyran-2-yloxy)-but-2-ynyl] amine (292 mg, 0.61 mmol) was stirred in 1 N HCl ethyl ether (6 mL) at room temperature for one hour. The mixture appeared two layers. A small amount of dichloromethane was added. The resulting homogenous solution was stirred at room temperature for 17 hours. 5% aqueous sodium bicarbonate solution (20 mL) was added to quench the reaction. The mixture was extracted with dichloromethane (2×20 mL). The combined organic solution was washed with brine (2×30 mL), dried over sodium sulfate, concentrated. The residue was purified by flash column chromatography on silica gel (Biotage, 0-5% methanol/dichloromethane and 5% methanol/dichloromethane) to afford 81 mg of product in 34% yield. $^1$H-NMR (500 MHz, CDCl$_3$): δ 4.23 (t, J =2.0 Hz, 2 H), 3.62-3.56 (m, 20 H), 3.52-3.50 (m, 2 H), 3.47 (t, J=2.0 Hz, 2 H), 3.34 (s, 3 H), 2.70 (t, J=6.0 Hz, 2 H and OH), 2.56 (q, J=7.0 Hz, 2 H), 1.03 (t, J=7.0 Hz, 3 H).

Synthesis of Cyclohexyl-hydroxy-phenylacetic acid (11)

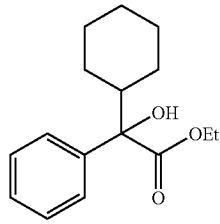 [SMILES: CCOC(=O)C(O)(c1ccccc1)C1CCCCC1]

A 250 mL round-bottom flask was charged with anhydrous THF (120 mL) at room temperature and then cooled to 0° C. with water/ice bath. Cyclohexylmagnesium chloride solution (2.0 M in ethyl ether) (56 mL, 112 mmol) was added. A solution of ethyl benzoylformate (14.89 g, 79.41 mmol) in THF (20 mL) was added dropwise over 30 minutes. More of THF (10 mL) was added to wash the addition funnel. The resulting mixture was stirred at 0° C. for 15 minutes, and then at room temperature for three hours. The reaction mixture was poured into saturated aqueous ammonium chloride (150 mL). Water (15 mL) was added. The mixture was concentrated to remove the organic solvents. The remaining solution was extracted with EtOAc (2×100 mL). The extraction was washed with brine, dried over sodium sulfate, concentrated to afford a slight green residue. The residue was purified with flash column chromatography on silica gel using 0-8% EtOAc/hexane (20 CV, 40 M column, biotage) to afford 14.955 g of product in 72% yield. $^1$H-NMR (400 MHz, CDCl$_3$).

Synthesis of 2-Cyclohexyl-2-Phenylglycolic Acid (12)

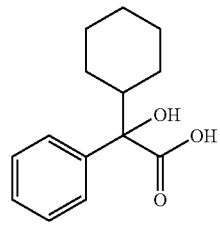 [SMILES: O=C(O)C(O)(c1ccccc1)C1CCCCC1]

To a solution of cyclohexyl-hydroxy-phenylacetic acid (1.04 g, 3.96 mmol) in methanol (20 mL) was added a 1 N NaOH (8 mL). The reaction mixture was allowed to warm to 80° C. and stirred for 3.5 hours. After cooling to room temperature, the mixture was extracted with ethyl ether. The combined organic solution was washed with brine, dried over sodium sulfate, and concentrated in vacuo to give crude product as a white solid. The solid was recrystallized with hexane and dichloromethane to afford 900 mg of 2-cyclohexyl-2-phenylglycolic acid in 97% yield. $^1$H-NMR (CDCl$_3$).

Synthesis of mPEG$_6$-Oxybutynin (16) (n=6)

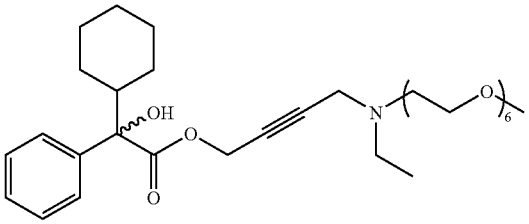

N-methyl morphinone (40 μL, 0.36 mmol) was added to a stirred solution of 2-cyclohexyl-2-phenylglycolic acid (12) (35.5 mg, 0.15 mmol) and 4-(mPEG$_6$ ethylamino)-but-2-yn-1-ol (8) (n=6) (45 mg, 0.12 mmol) in anhydrous DMF (2 mL) at room temperature. 1-Hydroxybenzotriazole (HOBt) (28.4 mg, 0.21 mmol) was added. The mixture was stirred at room temperature for 30 minutes, N,N'-dicyclohexylcarbodiimide (32.5 mg, 0.16 mmol) was added. The resulting mixture was stirred at room temperature for 20 hours. Water was added to quench the reaction. The mixture was extracted with EtOAc (3×15 mL). The combined organic solution was washed with brine (2×30 mL), dried over Na$_2$SO$_4$, and concentrated. The residue was purified with flash column chromatography on silica gel using 0-10% MeOH/dichloromethane to afford the product (16) (n=6) (25 mg). $^1$H-NMR (500 MHz, CDCl$_3$): δ 7.65-7.63 (m, 2 H), 7.35-7.32 (m, 2 H), 7.27-7.25 (m, 1 H), 4.84-4.70 (m, 2 H), 3.65-3.58 (m, 18 H), 3.55-3.52 (m, 4 H), 3.47 (m, 2 H), 3.37 (s, 3 H), 2.63 (t, J=6.0 Hz, 2 H), 2.49 (q, J=7.0 Hz, 2 H), 2.25 (m, 1 H), 2.04 (br, s, 1 H), 1.79-1.77 (m, 1 H), 1.64 (m, 1 H), 1.54-1.52 (m, 2 H), 1.46-1.38 (m, 1 H), 1.35-1.26 (m, 1 H), 1.20-1.06 (m, 4 H), 1.02 (t, J=7.0 Hz, 3 H). LC-MS: 608.3 (MH$^+$).

Synthesis of Cyclohexyl Hydroxy Phenyl Acetic Acid 4-Hydroxy But-2-ynyl Ester (20)

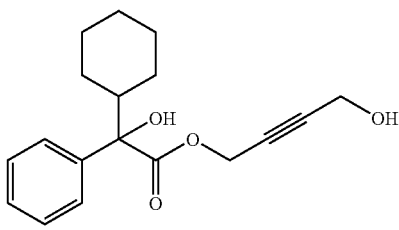 [SMILES: O=C(OCC#CCO)C(O)(c1ccccc1)C1CCCCC1]

Method I:

HOBt (135.7 mg, 1.0 mmol) was added a stirred solution of 2-cyclohexyl-2-phenylglycolic acid 12 (240 mg, 1.0 mmol) and 2-butyne-1,4-diol (87 mg, 1.0 mmol) in anhydrous DMF (7.0 mL), cooled to 0° C. N-methyl morphinone (0.25 mL, 2.26 mmol) was added. The resulting mixture was stirred at 0° C. for 30 minutes. DCC (216.5 mg, 1.05 mmol) was added.

The resulting mixture was stirred at 0° C. for 30 minutes, and then at room temperature for 21.5 hours. EtOAc (20 mL) was added and the white precipitate removed by filtration. The organic solution was separated and the aqueous solution was extracted with EtOAc (2×25 mL). The combined organic solution was washed with brine, dried over Na$_2$SO$_4$, concentrated. The residue was separated with flash column chromatography on silica gel using 0-20% EtOAc/hexane to afford the product (20) (50 mg, 17% yield), along with cyclohexyl phenyl acetic acid 4-(2-cyclohexyl-2-hydroxy-2-phenyl acetoxy)-but-2-ynyl ester (26) (99 mg, 37% yield) (as shown in the following structure).

side product (26)

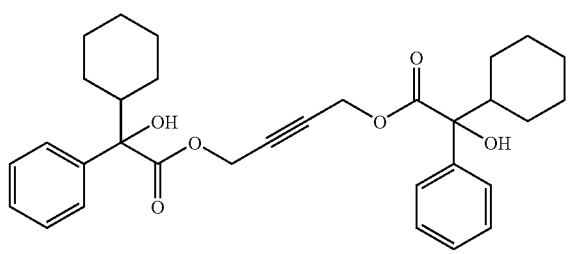

$^1$H-NMR (500 MHz, CDCl$_3$) for compound (20): δ 7.66-7.64 (m, 2 H), 7.37-7.34 (m, 2 H), 7.30-7.27 (m, 1 H), 4.87-4.72 (m, 2H), 4.29-4.27 (m, 2 H), 3.57 (s, 1 H), 2.29-2.23 (m, 1 H), 1.82-1.79 (m, 1 H), 1.66-1.64 (m, 2 H), 1.54-1.51 (m, 1 H), 1.47-1.39 (m, 1 H), 1.37-1.29 (m, 1 H), 1.22-1.07 (m, 4 H). LC-MS: 325.1 (M+Na$^+$).

$^1$H-NMR (500 MHz, CDCl$_3$) for the side product—cyclohexyl phenyl acetic acid 4-(2-cyclohexyl-2-hydroxy-2-phenyl acetoxy)-but-2-ynyl este (26): δ 7.64-7.62 (m, 4 H), 7.36-7.3 (m, 4 H), 7.30-7.26 (m, 2 H), 4.84-4.68 (m, 4 H), 3.543 (s, 1 H), 3.535 (s, 1 H), 2.24 (m, 2 H), 1.82-1.79 (m, 2 H), 1.66-1.65 (m, 4 H), 1.52-1.47 (m, 2 H), 1.44-1.38 (m, 2 H), 1.22-1.07 (m, 8 H). LC-MS: 541.2 (M+Na$^+$).

Method II:

A solution of 2-cyclohexyl-2-phenylglycolic acid (12) (579 mg, 2.47 mmol) and 1,1'-carbonyldiimidazole (462 mg, 2.85 mmol) was stirred at 50° C. for 5 hours, cooled to room temperature. The solution was added to a stirred solution of 2-butyne-1,4-diol (1) (1.0085 g, 11.60 mmol) and triethylamine (2.0 mL, 14.28 mmol) in anhydrous DMF (15 mL) at −70° C. (isopropanol/dry ice) over 5 minutes. The resulting mixture was stirred at −70° C. for one hour. The cooling bath was removed and the reaction mixture was allowed to warm up to room temperature and continued to stir at room temperature for 18 hours. Water was added to quench the reaction. The mixture was extracted with ethyl acetate (3×25 mL). The combined organic solution was washed with brine (2×50 mL), dried over anhydrous sodium sulfate, concentrated. The residue was separated with flash column chromatography on silica gel using 0-5% methanol in dichloromethane to afford the product (20) (509 mg) in 68% yield, along with the side product—cyclohexyl phenyl acetic acid 4-(2-cyclohexyl-2-hydroxy-2-phenyl acetoxy)-but-2-ynyl ester (26) (129 mg, 20% yield).

Synthesis of Cyclohexyl Hydroxy Phenyl Acetic Acid 4-Methanesulfonyloxy But-2-ynyl Ester (21) (X=OMs)

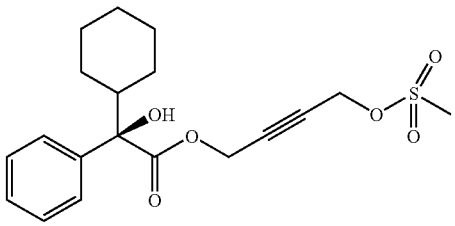 [SMILES: CS(=O)(=O)OCC#CCOC(=O)[C@](O)(c1ccccc1)C1CCCCC1]

Cyclohexyl-hydroxy-phenyl-acetic acid 4-hydroxy but-2-ynyl ester (20) (277 mg, 0.92 mmol) was dissolved in dichloromethane (5 mL), cooled to 0° C. Triethylamine (0.2 mL, 1.43 mmol) was added. Methanesulfonyl chloride (75 µL, 0.96 mmol) was added dropwise with syringe. The resulting mixture was stirred at 0° C. for 40 minutes, at room temperature for 19 hours. Water was added to quench the reaction. Small of saturated sodium chloride (10 mL) was added. The organic phase was separated and the aqueous phase was extracted with dichloromethane (15 mL). The combined organic solution was washed with brine, dried over anhydrous sodium sulfate, concentrated. The residue was separated with flash column chromatography on silica gel using 5-50% ethyl acetate in hexane to afford the product (21) (98 mg) in 28% yield, along with a side product, cyclohexy-hydroxy phenyl acetic acid 4-[4-(2-cyclohexy-2-hydroxy-2-phenyl-acetoxy)-but-2-ynyl ester 27 (117 mg, 43% yield) (as shown in the following structure).

side product (27)

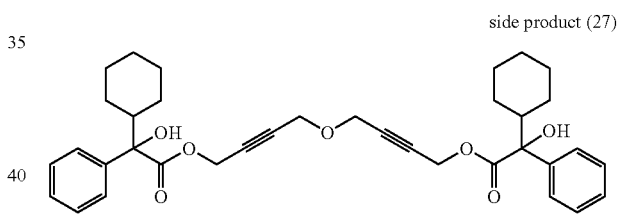

$^1$H-NMR (500 MHz, CDCl$_3$) for compound 20: δ 7.63-7.61 (m, 2 H), 7.36-7.33 (m, 2 H), 7.30-7.26 (m, 1 H), 4.86-4.76 (m, 4 H), 3.54 (s, 1 H), 2.99 (s, 3 H), 2.27-2.22 (m, 1 H), 1.82-1.79 (m, 1 H), 1.66-1.64 (m, 2 H), 1.50-1.39 (m, 2 H), 1.37-1.27 (m, 1 H), 1.21-1.06 (m, 4 H). LC-MS: 398.1 (M$^+$+ 18), 403 (M+Na$^+$).

$^1$H-NMR (500 MHz, CDCl$_3$) for the side product 27: δ 7.66-7.64 (m, 4 H), 7.37-7.34 (m, 4 H), 7.30-7.26 (m, 2 H), 4.89-4.72 (m, 4 H), 4.13 (t, J=2.0 Hz, 4 H), 3.58 (s, 2 H), 2.30-2.24 (m, 2 H), 1.83-1.80 (m, 2 H), 1.66-1.65 (m, 4 H), 1.54-1.52 (m, 2 H), 1.48-1.40 (m, 2 H), 1.38-1.29 (m, 2 H), 1.22-1.08 (m, 8 H).

Synthesis of mPEG$_4$-Oxybutynin (16) (n=4)

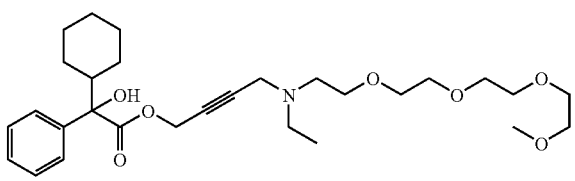 [SMILES: CCN(CC#CCOC(=O)C(O)(c1ccccc1)C1CCCCC1)CCOCCOCCOCCOC]

A mixture of the mesylate (21) (X=OMs) (98 mg, 0.26 mmol) and mPEG$_4$-NHEt (6) (n=4) (purity: 90.6%) (97 mg, 0.38 mmol) and potassium carbonate (113.8 mg, 0.82 mmol) in acetonitrile (3 mL) was stirred at room temperature for 65 hours. The reaction mixture was filtered and washed with dichloromethane. The solution was concentrated at reduced pressure. The residue was purified with flash column chromatography on silica gel using 0-10% methanol in dichloromethane to afford the product (104 mg) in 77% yield as oil. $^1$H-NMR (500 MHz, CDCl$_3$): δ 7.65-7.64 (m, 2 H), 7.35-7.32 (m, 2 H), 7.28-7.25 (m, 1 H), 4.84-4.70 (m, 2 H), 3.66-3.59 (m, 11 H), 3.56-3.53 (m, 4 H), 3.46 (m, 2 H), 3.38 (s, 3 H), 2.62 (t, J=6.0 Hz, 2H), 2.49 (q, J=7.0 Hz, 2 H), 2.28-2.23 (m, 1 H), 1.80-1.77 (m, 1 H), 1.64 (m, 1 H), 1.55-1.52 (m, 2 H), 1.47-1.38 (m, 1 H), 1.35-1.26 (m, 1 H), 1.20-1.06 (m, 4 H), 1.02 (t, J=7.0 Hz, 3H). LC-MS: 520.2 (MH$^+$).

Structure (16) having a variety of oligomer sizes can be prepared using the same approach but substituting an oligomer having a different size.

What is claimed is:

1. A compound having the following structure:

$$R^2-\underset{R^3}{\underset{|}{\overset{R^1}{\overset{|}{C}}}}-\overset{O}{\overset{\|}{C}}-O-L^2-\underset{R^5}{\overset{X-POLY}{N}}$$

wherein:
R$^1$ is selected from the group consisting of cyclopentyl, 1-hydroxyl cyclopentyl, cyclohexyl and phenyl;
R$^2$ is selected from the group consisting of —H and —OH;
R$^3$ is selected from the group consisting of cyclopentyl, 1-hydroxyl cyclopentyl, cyclohexyl and phenyl;
L$^2$ is selected from the group consisting of hydrocarbon linkers of 2-4 carbons, heterocyclo linkers, and biheterocyclo linkers;
R$^5$ is selected from the group consisting of —CH$_3$ and —CH$_2$CH$_3$;
X is a spacer moiety; and
POLY is a water-soluble, non-peptidic oligomer,
and charged species of the compound.

2. The compound of claim 1, wherein R$^1$ is cyclohexyl, R$^2$ is —OH, and R$^3$ is phenyl.

3. The compound of claim 1, wherein L$^2$ is —CH$_2$—C≡C—CH$_2$—.

4. The compound of claim 1, having the following structure:

wherein (n) is 1-30.

5. The compound of claim 1, wherein the water-soluble, non-peptidic oligomer is a poly(alkylene oxide).

6. The compound of claim 5, wherein the poly(alkylene oxide) is a poly(ethylene oxide).

7. The compound of claim 1, wherein the spacer moiety is a covalent bond.

8. The compound of claim 1, wherein the water-soluble, non-peptidic oligomer has between 1 and 30 monomers.

9. The compound of claim 8, wherein the water-soluble, non-peptidic oligomer has between 1 and 10 monomers.

10. The compound of claim 5, wherein the poly(alkylene oxide) includes an alkoxy or hydroxy end-capping moiety.

11. The compound of claim 1, wherein the spacer moiety is an ether linkage.

12. The compound of claim 1, wherein the spacer moiety is an ester linkage.

13. The compound of claim 1, wherein the spacer moiety is an amine linkage.

14. A composition comprising a compound of claim 1, and optionally, a pharmaceutically acceptable excipient.

15. A composition of matter comprising a compound of claim 1, wherein the compound is present in a dosage form.

16. The compound of claim 1, having the following structure:

* * * * *